US011969711B2

(12) United States Patent
Kim et al.

(10) Patent No.: US 11,969,711 B2
(45) Date of Patent: Apr. 30, 2024

(54) CARBON-BASED, PRECIOUS METAL-TRANSITION METAL COMPOSITE CATALYST AND PREPARATION METHOD THEREFOR

(71) Applicant: HANWHA SOLUTIONS CORPORATION, Seoul (KR)

(72) Inventors: Jeong Kwon Kim, Daejeon (KR); Sun Woo Yook, Daejeon (KR); Bong Sik Jeon, Daejeon (KR); Wan Jae Myeong, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 149 days.

(21) Appl. No.: 17/417,377

(22) PCT Filed: Dec. 10, 2019

(86) PCT No.: PCT/KR2019/017381
§ 371 (c)(1),
(2) Date: Jun. 23, 2021

(87) PCT Pub. No.: WO2020/141748
PCT Pub. Date: Jul. 9, 2020

(65) Prior Publication Data
US 2022/0062868 A1 Mar. 3, 2022

(30) Foreign Application Priority Data
Dec. 31, 2018 (KR) .................. 10-2018-0173960

(51) Int. Cl.
*B01J 23/62* (2006.01)
*B01J 27/20* (2006.01)
(Continued)

(52) U.S. Cl.
CPC ............ *B01J 23/626* (2013.01); *B01J 27/20* (2013.01); *B01J 35/023* (2013.01);
(Continued)

(58) Field of Classification Search
CPC ........ B01J 23/626; B01J 27/20; B01J 35/023; B01J 35/1009; B01J 35/1014;
(Continued)

(56) References Cited

U.S. PATENT DOCUMENTS 3,804,779 A * 4/1974 Kent ..................... B01J 23/44
564/465
4,447,665 A * 5/1984 Wennerberg .............. C07C 5/41
585/419
(Continued)

FOREIGN PATENT DOCUMENTS

| CN | 101982236 A | 3/2011 |
|---|---|---|
| CN | 103785418 A | 5/2014 |

(Continued)

OTHER PUBLICATIONS

English Translation of Written Opinion for PCT/KR2019/017381. (Year: 2020).*

*Primary Examiner* — Patricia L. Hailey
(74) *Attorney, Agent, or Firm* — Harvest IP Law, LLP

(57) ABSTRACT

The present invention relates to a carbon-based precious metal-transition metal composite catalyst and a preparation method therefor, and more particularly, to a catalyst synthesis method in which, when preparing a high-content precious metal-transition metal composite catalyst, a catalyst having uniform particles and composition can be prepared, and cyclohexane dimethanol (CHDM) is efficiently produced by the hydrogenation reaction of cyclohexane dicarboxylic acid (CHDA) in an aqueous solution. Provided is a method for preparing a carbon-based precious metal-transi-
(Continued)

tion metal composite catalyst, wherein, in the carbon-based precious metal-transition metal composite catalyst, the precious metal is included in an amount of 10-20 parts by weight, and the transition metal is included in an amount of 10-20 parts by weight based on 100 parts by weight of the composite catalyst, and thus a total amount of the precious metal-transition metal is 20-40 parts by weight based on 100 parts by weight of the composite catalyst.

21 Claims, 3 Drawing Sheets

(51) Int. Cl.
  B01J 35/02 (2006.01)
  B01J 35/10 (2006.01)
  B01J 37/03 (2006.01)
  B01J 37/04 (2006.01)
  B01J 37/06 (2006.01)
  B01J 37/08 (2006.01)
  B01J 37/18 (2006.01)
  C07C 29/149 (2006.01)
(52) U.S. Cl.
  CPC ....... *B01J 35/1009* (2013.01); *B01J 35/1014* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 35/1057* (2013.01); *B01J 35/1061* (2013.01); *B01J 37/035* (2013.01); *B01J 37/04* (2013.01); *B01J 37/06* (2013.01); *B01J 37/08* (2013.01); *B01J 37/18* (2013.01); *C07C 29/149* (2013.01)
(58) Field of Classification Search
  CPC ................ B01J 35/1019; B01J 35/1023; B01J 35/1028; B01J 35/1038; B01J 35/1042; B01J 35/1047; B01J 35/1057; B01J 35/1061; B01J 37/035; B01J 37/04; B01J 37/06; B01J 37/08; B01J 37/18; C07C 29/149
  USPC ........ 502/182, 185; 568/878, 880, 881, 884, 568/885
  See application file for complete search history.

(56) References Cited

U.S. PATENT DOCUMENTS

| 5,149,680 | A | * | 9/1992 | Kitson | B01J 23/688 502/313 |
| 5,478,952 | A | * | 12/1995 | Schwartz | C07B 31/00 568/885 |
| 6,376,414 | B1 | * | 4/2002 | Antons | C07B 41/02 568/864 |
| 7,126,034 | B2 | * | 10/2006 | Meng | C12C 11/02 568/885 |
| 9,108,895 | B2 | * | 8/2015 | Liu | C07C 29/149 |
| 2003/0114719 | A1 | * | 6/2003 | Fischer | C07C 29/177 568/885 |
| 2005/0176972 | A1 | * | 8/2005 | Fischer | B01J 21/18 549/326 |
| 2009/0131247 | A1 | | 5/2009 | Lo et al. | |

FOREIGN PATENT DOCUMENTS

| CN | 104549494 A | 4/2015 | |
| CN | 106423202 A | 2/2017 | |
| EP | 0147219 | * 7/1985 | .............. B01J 23/64 |
| JP | 2002275212 A | 9/2002 | |
| JP | 2017515656 A | 6/2017 | |
| KR | 20020040809 A | 5/2002 | |
| KR | 1020020075467 A | 10/2002 | |
| KR | 1020050072109 A | 7/2005 | |
| KR | 1020090064455 A | 6/2009 | |
| KR | 1020130081130 A | 7/2013 | |
| KR | 1020150109607 A | 10/2015 | |
| KR | 101578071 B1 | 12/2015 | |
| KR | 1020190081123 A | 7/2019 | |
| RU | 2675361 C1 | 12/2018 | |

* cited by examiner

CARBON-BASED, PRECIOUS METAL-TRANSITION METAL COMPOSITE CATALYST AND PREPARATION METHOD THEREFOR

CROSS-REFERENCE TO RELATED APPLICATIONS

This application is a National Stage of International Application No. PCT/KR2019/017381 filed Dec. 10, 2019, claiming priority based on Korean Patent Application No. 10-2018-0173960 filed Dec. 31, 2018.

TECHNICAL FIELD

The present invention relates to a carbon-based precious metal-transition metal composite catalyst on which a high-content metal having uniform composition is supported, and a preparation method therefor, and more particularly, to a precious metal-transition metal composite catalyst that efficiently produces cyclohexane dimethanol (CHDM) by a hydrogenation reaction of cyclohexane dicarboxylic acid (CHDA) in an aqueous solution, and a method for preparing the precious metal-transition metal composite catalyst having uniform composition and metal size even in a high metal content.

BACKGROUND ART

Cyclohexane dimethanol (CHDM, 1,4-cyclohexanedimethanol) is the basic raw material for the preparation of polyester or polyamide resins. CHDM is commercially prepared in Asia by SK NJC, which is a joint-venture firm established by SK Chemicals, Mitsubishi Corporation, and Shin Nippon Rika. Indorama [old name: Eastman] is dominating the entire markets all over the world. Currently, Indorama produces 100 KTA of CHDM and SK NJC produces 20 KTA of CHDM. It is known that SK NJC plans to increase the production to 60 KTA by additionally installing one production line in two existing production lines.

According to the known documents, there are three methods for preparing a CHDM using a purified terephthalic acid (RTA).

According to a first method, salt is produced by ionizing PTA with NaOH in an aqueous solution to increase PTA solubility and a hydrogenation reaction is performed. This synthesis method has an advantage of lowering the hydrogenation reaction temperature as the solubility of PTA increases at a low temperature (40-130° C.). However, after the reaction, a process of recovering Na$^+$ ions by neutralizing with HCl is additionally required. A residual Na Salt affects PETG polymerization after the reaction, and a brine solution containing NaCl incurs excessive wastewater treatment costs, which is disadvantageous in the costs of the production process.

According to a second method, dimethyl terephthalate (DMT) is prepared by esterifying PTA and CHDM is prepared through dimethyl cyclohexane dicarboxylate (DMCD). Since this process uses a Cu-based or Cr-based catalyst when preparing CHDM from DMCD, it is relatively inexpensive in terms of catalyst price. However, since this process is a three-step preparation process (PTA→DMT→DMCD→CHDM), it is disadvantageous in terms of process. In addition, since different solvents are used in the processes, a large amount of wastewater is generated and DMT, which is more expensive than PTA, is used as the raw material.

On the other hand, a third method is a process of preparing CHDM from PTA through CHDA. Since ruthenium, which is a precious metal, is used as an active metal in a CHDA hydrogenation reaction, it is disadvantageous in terms of catalyst price. However, since the final product CHDM can be obtained through the two-step process (PTA→CHDA→CHDM), it is determined that this process is advantageous in terms of cost reduction if the product cost is reduced through a reduction in process steps and the competitiveness of process technology is secured.

Therefore, the present invention proposes a method for synthesizing a catalyst that efficiently produces cyclohexane dimethanol (CHDM), which is a target dialcohol, by using cyclohexane dicarboxylic acid (CHDA) as a representative material of dicarboxylic acid.

Mechanism 1 shows a mechanism of reduction of a carbonyl group on a heterogeneous catalyst. A precious metal-transition metal composite catalyst is mainly used to convert a carbonyl group on a heterogeneous catalyst into alcohol. In the composite catalyst, the precious metal adsorbs hydrogen to form a metal-hydride, and the transition metal acts as a Lewis acid to polarize the carbonyl group. After that, the metal-hydride is bonded to the activated carbonyl group and converted into an alcohol. Therefore, the uniformity of precious metal-transition metal activity is required for efficient reduction of a carbonyl group in a heterogeneous catalyst.

[Mechanism 1]

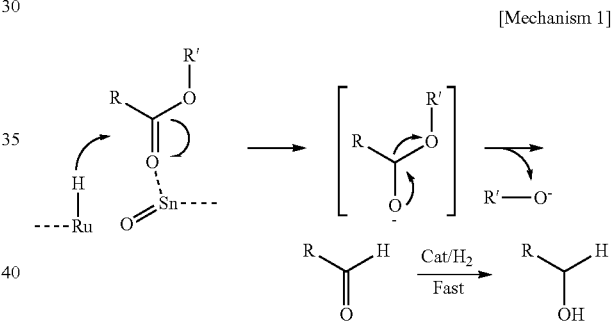

According to a preparing method, an ion-exchange method, an incipient-wetness impregnation method, a deposition-precipitation method, and the like may be used to prepare a carbon-based supported catalyst.

The ion-exchange method is a method in which a catalytically active phase is supported on a support by exchanging positive/anionic ions, which are active ingredients, with ions on the surface of the support. The ion-exchange method is mainly used to support metals on zeolite, silica, and silica-alumina. The ion-exchange method proceeds in a continuous step of ion diffusion, in which an active material moves to the surface of the support, and ion exchange on the surface. In order to prepare an efficient catalyst, it is necessary to repeatedly perform ion exchange several times, which increases the manufacturing time and thus increases the costs.

The incipient-wetness impregnation method is the most widely used method for preparing a supported catalyst. First, an active metal precursor is dissolved in a solvent corresponding to a total pore volume of a support. After that, the active metal solution is added to the dried support, absorbed, and dried to remove the solvent. Therefore, although the preparation of the catalyst is simple, there is a disadvantage in that the activity is deteriorated because the particles and composition of the catalyst are not uniform when a high-content metal-supported catalyst is prepared. In Chinese Patent Laid-Open No. 101982236, Zhang Xiaoou proposes Ru—Sn/OMC (OMC=ordered mesoporous carbon) as a CHDA-to-CHDM catalyst. The catalyst is prepared by supporting Ru and Sn chloride precursors through an incipient-wetness impregnation method and performing drying and reduction thereon. As described above, it is difficult to prepare a catalyst having a high content of 20 wt % or more through the preparation of the catalyst prepared by the incipient-wetness impregnation method. In addition, since chloride is highly corrosive, there is a disadvantage in that corrosion-resistant equipment is required in the drying and reduction process. Therefore, ease of manufacture in the preparation of the catalyst and a method for preparing a catalyst having a uniform active metal composition at a high content have to be secured.

The deposition-precipitation method is a catalyst preparing method in which an aqueous solution of an active ingredient and a precipitant react in a carbon support dispersion to form precipitates, and these are adsorbed and solidified on the surface of the support. Therefore, the deposition-precipitation method is reported as a method capable of supporting a large amount of active metal, compared with the existing incipient-wetness impregnation method and ion-exchange method, and it is known that the uniformity of the supported active phase is also high.

(Patent Literature 1) Korean Patent Application Publication No. 2002-0040809 (2002. May 30.)
(Patent Literature 2) Chinese Patent Laid-Open No. 103785418 (2014. May 14.)
(Patent Literature 3) Chinese Patent Laid-Open No. 106423202 (2017. Feb. 22.)
(Patent Literature 4) U.S. Patent Registration No. 2009-0131247 (2009. May 21.)

DESCRIPTION OF EMBODIMENTS

Technical Problem

The present invention aims to solve the above-described problems of the related art and the technical problems requested from the past.

An object of the present invention is to provide a precious metal-transition metal composite catalyst, in which a reaction rate and reaction efficiency are improved when dialcohol is produced from dicarboxylic acid with a long reaction time by using a carbon-based precious metal-transition metal composite catalyst on which a high-content metal having a uniform composition is supported, and a method for preparing a catalyst so that the composition and metal size of the catalyst are uniform even with a high content of metal.

Solution to Problem

In order to achieve the objects, a carbon-based precious metal-transition metal composite catalyst according to the present invention may include 10-20 parts by weight of the precious metal and 10-20 parts by weight of the transition metal based on 100 parts by weight of the composite catalyst, wherein a total amount of the precious metal-transition metal may be 20-40 parts by weight based on 100 parts by weight of the composite catalyst.

The entire active metal may include a precious metal and a transition metal. Preferably, ruthenium (Ru) may be provided as the precious metal, and tin (Sn) may be provided as the transition metal.

These metals may be denoted by 'Ru—Sn/C'. These metals may be prepared by a deposition-precipitation (DP) method and may be denoted by 'Ru—Sn/C-DP'.

According to an embodiment of the present invention, the precious metal-transition metal may be an active metal having a metal crystallite size of 1-20 nm. Preferably, the average size of the active metal may be 1-15 nm.

According to an embodiment of the present invention, the precious metal and the transition metal may be supported on the support in a range of 0.5-3 moles of the transition metal with respect to 1 mole of the precious metal. Preferably, the transition metal and the precious metal may be provided in the same molar ratio.

According to an embodiment of the present invention, an average particle size ($d_{50}$) of the precious metal-transition metal composite catalyst may be 3-50 μm.

According to an embodiment of the present invention, the precious metal-transition metal may form a homogeneous mixed phase.

According to an embodiment of the present invention, the carbon may include one or more selected from the group consisting of activated carbon, carbon black, graphite, graphene, ordered mesoporous carbon (OMC), and carbon nanotubes. Preferably, the precious metal may be ruthenium, and the transition metal may be tin.

According to an embodiment of the present invention, the carbon may have a specific surface area of 100-1,500 $m^2/g$ and a pore volume of 0.1-1.5 ml/g.

According to one preferred embodiment of the present invention, the carbon may have ordered mesopores of 2-25 nm, and may be ordered mesoporous carbon (OMC) having a three-dimensional rod-shaped or three-dimensional tube-shaped pore structure. That is, since the active metal is supported inside the carbon support arranged in a three-dimensional ordered mesoporous structure, the reaction rate can be improved due to higher catalytic activity, compared with an existing catalyst.

According to an embodiment of the present invention, the carbon support may be pretreated with an aqueous nitric acid ($HNO_3$) solution. In this case, the carbon support may include 1-50 parts by weight of nitric acid based on 100 parts by weight of the total aqueous solution.

According to an embodiment of the present invention, the pretreating may be performed at a temperature of 50-150° C. The pretreating may be performed for 1-10 hours. The pretreating may be performed before the active metal is supported.

On the other hand, the present invention provides a hydrogenation method for performing a hydrogenation reaction using a carbon-based precious metal-transition metal composite catalyst on which a high-content metal having a uniform composition is supported.

The hydrogenation reaction may be provided for the use of a hydrogenation catalyst for hydrogenating a carboxylic acid group to an alcohol group. Preferably, the hydrogenation reaction may include reducing a dicarboxylic acid group to a dialcohol group.

In addition, the hydrogenation reaction may reduce a carboxylic acid functional group, an aldehyde functional group, or a ketone functional group to an alcohol functional group.

According to an embodiment of the present invention, the hydrogenation reaction pressure may be 20-150 bar, the reaction temperature may be 140-280° C., and the reaction time may be 0.5-10 hours.

According to an embodiment of the present invention, the carboxylic acid may include one or more selected from the group consisting of oxalic acid, malonic acid, succinic acid, glutaric acid, adipic acid, pimelic acid, suberic acid, azelaic acid, sebacic acid, phthalic acid, isopthalic acid, cyclohexane dicarboxylic acid, and terephthalic acid According to an embodiment of the present invention, the aldehyde functional group may include one or more selected from the group consisting of formaldehyde, propionaldehyde, n-butylaldehyde, isobutylaldehyde, valeraldehyde, 2-methylbutylaldehyde, 3-methylbutylaldehyde, 2,2-dimethylpropionaldehyde, capronaldehyde, 2-methylvaleraldehyde, 3-methylvaleraldehyde, 4-methylvaleraldehyde, 2-ethylbutylaldehyde, 2,2-dimethylbutylaldehyde, 3,3-dimethylbutylaldehyde, caprylaldehyde, caprinealdehyde, and glutalaldehyde.

According to an embodiment of the present invention, the ketone functional group may include one selected from the group consisting of acetone, butanone, pentanone, hexanone, cyclohexanone, and acetophenone.

Advantageous Effects of Disclosure

As described above, in a carbon-based precious metal-transition metal composite catalyst, on which a high-content metal having a uniform composition is supported, and a preparation method therefor, a reaction rate and reaction efficiency may be improved when dialcohol is produced from dicarboxylic acid with a long reaction time, and the composition and metal size of the catalyst may be uniform even with a high content of metal.

BEST MODE

Figure 1:
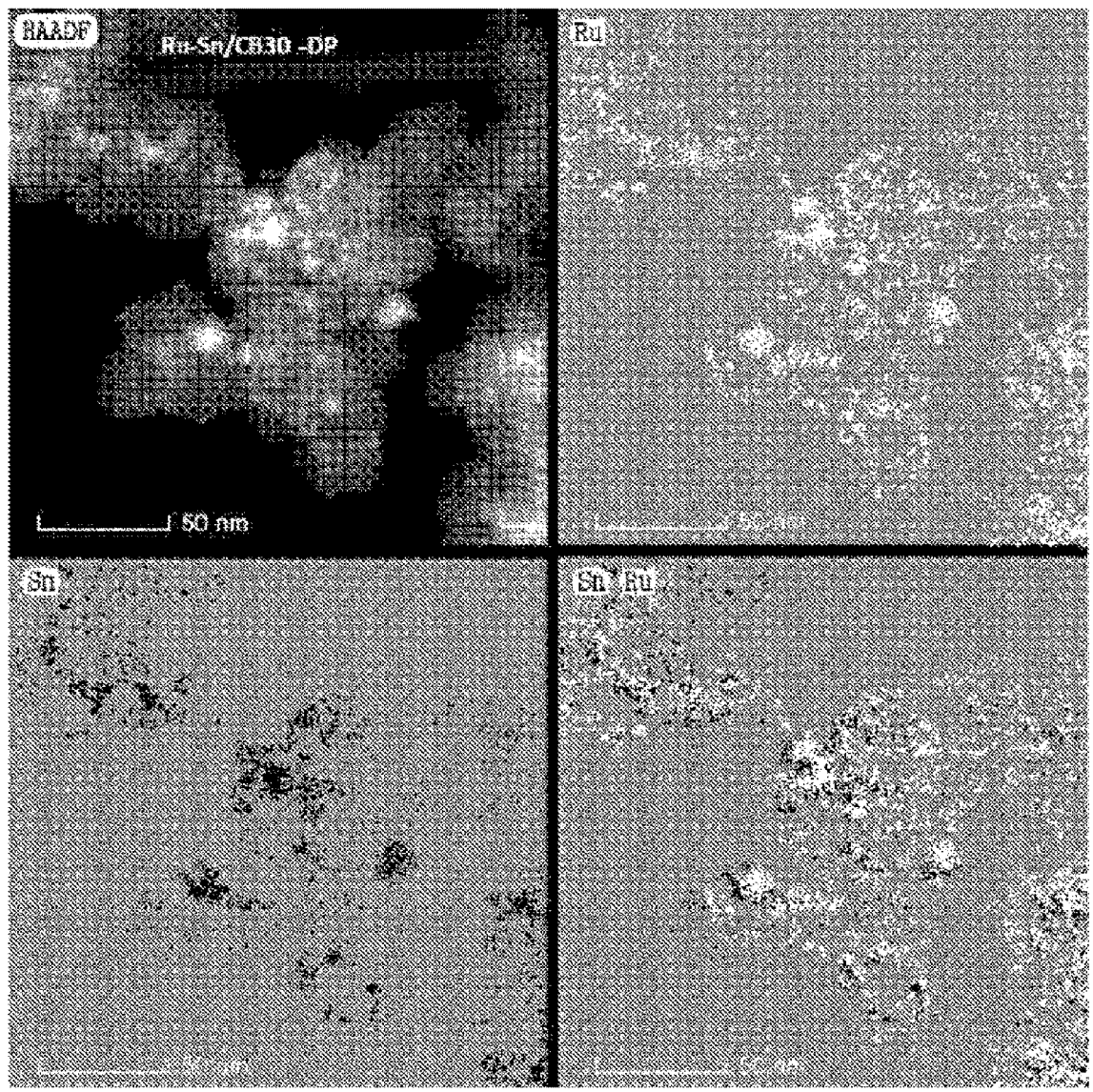
FIG. 1 is a scanning transmission electron microscope-energy dispersive X-ray spectroscopy (STEM-EDX) analysis result of a Ru—Sn/C-DP catalyst prepared by a deposition-precipitation method according to an embodiment of the present invention.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment.

Therefore, the following detailed description is not to be taken in a limiting sense, and the scope of the present invention is to be limited only by the appended claims and the entire scope of equivalents thereof, if properly explained.

In addition, unless otherwise specified in the present specification, the term "substitution" or "substituted" means that one or more hydrogen atoms in the functional groups of the present invention are substituted with one or more substituents selected from the group consisting of a halogen atom (—F, —Cl, —Br, or —I), a hydroxy group, a nitro group, a cyano group, an amino group, an amidino group, a hydrazine group, a hydrazone group, a carboxyl group, an ester group, a ketone group, a substituted or unsubstituted alkyl group, a substituted or unsubstituted alicyclic organic group, a substituted or unsubstituted aryl group, a substituted or unsubstituted alkenyl group, a substituted or unsubstituted alkynyl group, a substituted or unsubstituted heteroaryl group, and a substituted or unsubstituted heterocyclic group. These substituents may be linked to each other to form a ring.

In the present invention, unless otherwise specified, the term "substituted" means that a hydrogen atom is substituted with a substituent such as a halogen atom, a $C_1$-$C_{20}$ hydrocarbon group, a $C_1$-$C_{20}$ alkoxy group, and a $C_6$-$C_{20}$ aryloxy group.

In addition, unless otherwise specified, the term "hydrocarbon group" refers to a linear, branched, or cyclic saturated or unsaturated hydrocarbon group. The alkyl group, the alkenyl group, the alkynyl group, and the like may be linear, branched, or cyclic.

In addition, unless otherwise specified in the present specification, the term "alkyl group" refers to a $C_1$-$C_{30}$ alkyl group and the term "aryl group" refers to a $C_6$-$C_{30}$ aryl group. In the present specification, the term "heterocyclic group" refers to a group in which one to three heteroatoms selected from the group consisting of O, S, N, P, Si, and any combination thereof are contained in one ring. Examples of the heterocyclic group may include pyridine, thiophene, and pyrazine, but the present invention is not limited thereto.

In the detailed description of the present invention, the term "dicarboxylic acid" refers to an organic acid having two carboxylic acid functional groups in one molecule. For example, the molecular formula of the dicarboxylic acid is HOOC—R—COOH. In the present invention, R is preferably an alkyl group or an aryl group.

Hereinafter, embodiments of the present invention will be described with reference to the accompanying drawings, so that those of ordinary skill in the art can easily carry out the present invention.

According to the present invention, a carbon-based precious metal-transition metal composite catalyst on which a high-content metal having a uniform composition is supported may improve the efficiency of the reaction, such as improving the conversion reaction rate and stability of cyclohexane dicarboxylic acid (CHDA). In addition, the catalyst may be prepared so that the composition and metal size of the catalyst are uniform even with a high content of metal.

Hereinafter, the composition of the carbon-based precious metal-transition metal composite catalyst, on which the above-described high-content metal having a uniform composition is supported, and the method for preparing the composite catalyst will be described in more detail.

According to the present invention, the carbon-based precious metal-transition metal composite catalyst includes 10-20 parts by weight of a precious metal and 10-20 parts by weight of a transition metal based on 100 parts by weight of the composite catalyst, and thus the total amount of the precious metal-transition metal is 20-40 parts by weight based on 100 parts by weight of the composite catalyst.

One or more precious metals selected from the group consisting of palladium (Pd), rhodium (Rh), ruthenium (Ru), and platinum (Pt) may be included, but the present invention is not limited thereto. The precious metal may be included in an amount of 1-20 parts by weight based on 100 parts by weight of the total composite catalyst. Preferably, the precious metal may be included in an amount of 10-15 parts by weight.

When the amount of the precious metal is less than the above range, there may be a problem that it is difficult to expect the target activity of the catalyst, and when the amount of the precious metal is greater than the above range, the price of the catalyst increases and it is difficult to obtain a high degree of dispersion of metal components during the preparation of the catalyst. Therefore, the above range is preferable.

The transition metal may include one or more transition metals selected from the group consisting of tin (Sn), iron (Fe), rhenium (Re), and gallium (Ga), but the present invention is not limited thereto. The transition metal may be included in an amount of 1-20 parts by weight based on 100 parts by weight of the total composite catalyst. Preferably, the transition metal may be included in an amount of 10-15 parts by weight.

When the amount of the transition metal is less than the above range, the conversion efficiency of the reaction decreases or the selectivity of the target product decreases. Thus, separation and recovery costs in the process may be used excessively. When the amount of the transition metal is greater than the above range, it is not efficient due to the generation of many by-products. Therefore, the above range is preferable.

In addition, in the present invention, the precious metal and the transition metal are included as the entire active metals. Preferably, ruthenium (Ru) may be provided as the precious metal, and tin (Sn) may be provided as the transition metal. This is also denoted by 'Ru—Sn/C'. Furthermore, since the precious metal and the transition metal are prepared by the DP method, the precious metal and the transition metal may be denoted by 'Ru—Sn/C-DP'.

According to the present invention, the precious metal-transition metal is an active metal having a metal crystallite size of 1-20 nm. Preferably, the active metal has a metal crystallite size 1-15 nm. When the metal crystallite size is greater than 20 nm, there is a problem in that the conversion efficiency is low and the production efficiency is reduced. Therefore, the above range is preferable.

In the composite catalyst, the precious metal and the transition metal are supported so that the molar ratio of the transition metal to the precious metal is in a range of 0.5-3 moles of the transition metal with respect to 1 mole of the precious metal. More preferably, the precious metal and the transition metal are provided in the same molar ratio. When the mole ratio of transition metal with respect to 1 mole of the precious metal is greater than 3, it is difficult to expect high conversion efficiency of CHDA due to the small production amount of metal-hydride. When the mole ratio of the transition metal with respect to 1 mole of the precious metal is less than 0.5, the number of metal sites that can polarize the carbonyl group is small, and thus the target selectivity cannot be obtained. Therefore, the above range is preferable.

In the catalyst, the average particle size ($d_{50}$) of the carbon-based precious metal-transition metal composite catalyst is 3-50 μm. When the particle size of the catalyst is less than the above range, the catalyst passes through a filtering membrane in a recycling process, causing the loss of the catalyst, and thus there may be a cost problem due to the purity of the product and the loss of the catalyst. When the particle size of the catalyst is greater than the above range, there may be a problem in that the efficiency of the catalyst decreases due to a low degree of dispersion in a reaction medium.

The precious metal-transition metal, which is the active metal of the composite catalyst, forms a homogeneous mixed phase. In the heterogeneous active metals of the catalyst (Ru—Sn/C-DP), for example, ruthenium (Ru) or tin (Sn) does not exist independently and forms a homogeneous mixed phase. In particular, by using a DP method, an aqueous solution of an active ingredient and a precipitant react in an excess carbon support dispersion to form precipitates, and these are adsorbed and solidified on the surface of the support to provide a mixed phase having a uniform composition of the active phase.

In a bimetallic catalyst, there is a literature reporting that a uniform composition of metal has a correlation with catalytic activity (Non-Patent Literature: J. Mol. Catal A-Chem 2015, 410, 184). Therefore, high uniformity between two metals is essential in order to obtain excellent catalytic activity at the same amount of metal supported. In the composite catalyst, the precious metal adsorbs hydrogen to generate metal-hydrides, and the transition metal acts as a Lewis acid to polarize a carbonyl group. After that, since the metal-hydride is adsorbed to the activated carbonyl group and converted into alcohol, the uniformity of the precious metal-transition metal active phase is necessarily required for the efficient reduction of carbonyl group. Therefore, the catalyst according to the present invention provides the precious metal-transition metal active phase of the uniform composition, thereby improving the efficiency of the reaction.

Next, the carbon support is not particularly limited. One or more selected from the group consisting of activated carbon, carbon black, graphite, graphene, ordered mesoporous carbon (OMC), and carbon nanotubes may be used as the carbon support. Preferably, the carbon support may be carbon black having a high ratio of mesopores among the total pores. In a specific example, the activated carbon may be SX ULTRA, CGSP, PK1-3, SX 1G, DRACO S51HF, CA-1, A-51, GAS 1240 PLUS, KBG, CASP, and SX PLUS, and the carbon black may be BLACK PEARLS, ELFTEX, VULCAN, MOGUL, MONARCH, EMPEROR, and REGAL. However, the present invention is not limited thereto.

According to the present invention, the carbon in the carbon support may be 50% or more in a volume ratio of mesopores having a pore size of 2-50 nm in the total pores. Preferably, the carbon in the carbon support is 70% or more in a volume ratio of mesopores among the total pores. More preferably, the carbon in the carbon support may be 75% or more in a volume ratio of mesopores among the total pores. In this case, when the volume ratio of the mesopores is less than 50%, there may be micro-transfer rate problems in the carbon support of the reactant and the product. When the average size of the pores is greater than 50 nm, the physical strength of the support may be weak. Therefore, the above range is preferable.

In addition, according to the present invention, the carbon includes ordered mesoporous carbon (OMC) having a specific surface area (BET) of 100-1,500 $m^2/g$. Preferably, the carbon includes ordered mesoporous carbon (OMC) having a specific surface area (BET) of 200-1,000 $m^2/g$. In this case, when the specific surface area of the carbon is less than 100 $m^2/g$, high dispersion of active metals may be difficult. When the specific surface area of the carbon is greater than 1,500 $m^2/g$, the ratio of the mesopores may decrease. Therefore, the above range is preferable.

Furthermore, in some cases, the carbon support of the catalyst according to the present invention includes micropores at an appropriate ratio in addition to the mesoporosity of a medium size. Preferably, the volume ratio of the micropores in the total pores may be 0-25%. In this case, when the volume ratio of the micropores is greater than 25%, there may be micro-transfer rate problems in the carbon support of the reactant and the product. Therefore, the above range is preferable.

On the other hand, the present invention provides a method for preparing a carbon-based precious metal-transition metal composite catalyst, wherein a carbon support is pretreated with an aqueous nitric acid ($HNO_3$) solution once or more times.

According to the present invention, a process of pretreating the carbon support with the aqueous nitric acid ($HNO_3$) solution once or more times is performed. The aqueous nitric acid ($HNO_3$) solution may include 1-50 parts by weight of nitric acid based on 100 parts by weight of the entire aqueous solution. Preferably, the aqueous nitric acid ($HNO_3$) solution may be an aqueous solution including 5-40 parts by weight of nitric acid based on 100 parts by weight of the entire aqueous solution. More preferably, the aqueous nitric acid ($HNO_3$) solution may be an aqueous solution including 5-35 parts by weight of nitric acid based on 100 parts by weight of the entire aqueous solution.

More specifically, when the pretreatment is performed with less than 1 part by weight of nitric acid based on 100 parts by weight of the entire aqueous solution, it may be difficult to expect the desired activity of the catalyst. When the pretreatment is performed with 50 parts by weight or more of nitric acid based on 100 parts by weight of the entire aqueous solution, the increase in the acidity of the surface of the carbon support and the poisoning of the active metal by oxygen functional groups may cause the reduction in the activity of the catalyst and the collapse of the carbon support structure. Therefore, the above range is preferable.

According to an embodiment of the present invention, the pretreatment process may be performed in a temperature range of 70-150° C., and preferably 80-110° C. In this case, when the temperature of the pretreatment process is less than 70° C., the introduction of oxygen functional groups into the surface of the carbon support may be lowered. When the temperature of the pretreatment process is greater than 150° C., the carbon support structure may collapse. Therefore, the above range is preferable.

On the other hand, the composite catalyst according to the present invention is used in the hydrogenation reaction, and the hydrogenation reaction provides a hydrogenation method for converting a dicarboxylic acid group into a dialcohol group.

The hydrogenation reaction may be performed at a temperature of 200-300° C. for 2-8 hours at a pressure of 50-150 bar. Preferably, the hydrogenation reaction of the CHDA may be performed at a temperature of 230-270° C. and a pressure of 70-130 bar. In this case, when the temperature is less than 200° C., the reaction rate is not sufficient, and thus the reaction rate is lower than the desired CHDM yield. Therefore, it is not preferable. When the temperature is greater than 300° C., side reactions such as the decomposition reaction of the reactant and the product may occur. When the pressure is less than 50 bar, hydrogen participating in the hydrogenation reaction of the CHDA is not sufficiently present in the solvent, and thus there is a problem that the catalytic activity decreases. Even when the hydrogenation reaction pressure is greater than 150 bar, an effect of improving the reaction rate is no longer obtained. Therefore, it is disadvantageous in terms of costs. Most preferably, the hydrogenation reaction temperature may be 200-250° C., the reaction pressure may be 90-110 bar, and the reaction time may be 2-6 hours.

The hydrogenation reaction may be performed in various reactors. Preferably, the hydrogenation reaction may be performed in a batch reactor, a continuous stirred tank reactor (CSTR), or a loop reactor.

According to an embodiment of the present invention, the catalyst may be used in a hydrogenation reaction for converting a carboxylic acid group into an alcohol group. Preferably, the catalyst may be used in a reduction reaction for hydrogenating a dicarboxylic acid functional group to a dialcohol functional group. For example, the catalyst may be used in a method for hydrogenating a carboxylic acid functional group, an aldehyde functional group, or a ketone functional group to an alcohol functional group.

In a specific example of the present invention, the cyclohexane dimethanol (CHDM) was produced through the hydrogenation reaction of the cyclohexane dicarboxylic acid (CHDA) on the precious metal-transition metal composite catalyst. At this time, the conversion rate of the CHDA converted through the hydrogenation reaction may be 95-99.9%, and the yield of the produced CHDM may be 85-99%.

The carboxylic acid is not particularly limited and may include, for example, oxalic acid, malonic acid, succinic acid, glutaric acid, adipic acid, pimelic acid, suberic acid, azelaic acid, sebacic acid, phthalic acid, isopthalic acid, terephthalic acid, formic acid, acetic acid, caproic acid, caprylic acid, lauric acid, myristic acid, palmitic acid, stearic acid, isostearylic acid, oleic acid, maleic acid, adipic acid, sebacic acid, cyclohexane carboxylic acid, and benzoic acid.

In addition, examples of the aldehydes having the aldehyde functional group may include formaldehyde, propionaldehyde, n-butylaldehyde, isobutylaldehyde, valeraldehyde, 2-methylbutylaldehyde, 3-methylbutylaldehyde, 2,2-dimethylpropionaldehyde, capronaldehyde, 2-methylvaleraldehyde, 3-methylvaleraldehyde, 4-methylvaleraldehyde, 2-ethylbutylaldehyde, 2,2-dimethylbutylaldehyde, 3,3-dimethylbutylaldehyde, caprylaldehyde, caprinealdehyde, and glutalaldehyde.

In addition, examples of the ketones having the ketone functional group may include acetone, butanone, pentanone, hexanone, cyclohexanone, and acetophenone.

On the other hand, according to an embodiment of the present invention, a carbon-based precious metal-transition metal composite catalyst may be prepared by the following preparation method.

The preparation method may include the steps of: (a) preparing a support dispersion in which a carbon support is dispersed in a solvent; (b) adding a precious metal-transition metal precursor aqueous solution and a precipitant to the support dispersion, supporting a metal oxide or a metal hydrate on the carbon support, and performing precipitating thereon; and (c) reducing and passivating the precipitate. In this case, the carbon-based precious metal-transition metal composite catalyst may include 10-20 parts by weight of the precious metal and 10-20 parts by weight of the transition metal based on 100 parts by weight of the composite catalyst, and thus the total amount of the precious metal-transition metal may be 20-40 parts by weight based on 100 parts by weight of the composite catalyst.

The carbon support is dispersed in a solvent and stirred at 60-100° C. for 30 minutes to 2 hours. The carbon support is stirred at 80° C. for 1 hour. The support may be at least one selected from the group consisting of activated carbon, carbon black, graphite, graphene, OMC, and carbon nanotubes. However, the present invention is not limited thereto.

Distilled water is provided as the solvent, and high purity water such as ion-exchanged water or deionized water (DIW) is provided as the distilled water. When the distilled water to be used contains impurities, the impurities may adhere to the catalyst, which may reduce the activity of the catalyst.

The precious metal may include one or more selected from the group consisting of palladium (Pd), rhodium (Rh), ruthenium (Ru), and platinum (Pt) in the form of a precursor. In this case, any commonly used precious metal can be used, and the precious metal is not particularly limited. The precious metal may be preferably ruthenium (Ru). The ruthenium precursor may include one or more selected from ruthenium chloride, acetylacetonate, iodide, oxide, and nitrosyl nitrate (nitrosyl nitrate solution) precursors. The ruthenium precursor may preferably include ruthenium chloride.

The transition metal may include at least one selected from the group consisting of tin (Sn), iron (Fe), rhenium (Re), and gallium (Ga) in the form of a precursor. The transition metal may be preferably tin (Sn). In addition, the tin precursor may include at least one selected from tin chloride, nitride, bromide, oxide, or acetate precursor. The tin precursor may preferably include tin chloride.

When the amount of the precious metal and the transition metal is less than the above range, there may be a problem that the conversion efficiency is reduced, and thus it is difficult to expect the target activity of the catalyst. When the amount of the precious metal is greater than the above range, the price of the catalyst increases and it is difficult to obtain a high degree of dispersion of metal components during the preparation of the catalyst. Therefore, the above range is preferable.

According to an embodiment of the present invention, an acidic solution may be provided so as to completely dissolve the metal precursor. Preferably, hydrochloric acid may be provided, but the present invention is not limited thereto. The precious metal precursor and the transition metal precursor are added to an aqueous solution containing hydrochloric acid and are then stirred. The stirring is performed for about 20-40 minutes. This is added again to the carbon dispersion, in which the carbon support is supported, to prepare a precious metal-transition metal-carbon support mixed solution Precious metal-transition metal oxide or hydrate is precipitated on the carbon support through pH control.

According to an embodiment of the present invention, the precipitation is performed at a temperature of 0-100° C., and preferably 60-80° C. The precipitant for pH control may include an alkaline solution, and may include one or more selected from the group consisting of hydroxide ($OH^-$), carbonate ($CO_3^{2-}$), and urea. In this case, any commonly used alkaline solution may be used, and the alkaline solution is not particularly limited. The precipitant may preferably include ammonium hydroxide.

After the precipitation, the pH of the solution finally becomes about 6. The precipitation may be performed in an environment of pH 3 or higher, and preferably pH 3-7, by addition of an aqueous alkali solution or electrochemical means.

After the precipitation is completed, the precipitation solution is filtered to recover the precipitate. The recovered precipitate is washed several times with distilled water of 80° C. or higher to remove remaining organic/inorganic materials. After that, the catalyst may be prepared by drying at about 100° C. and reducing in a hydrogen atmosphere at a temperature of 300-600° C. In addition, as described above, the optimum activity may be exhibited when the reduction temperature is 200 to 600° C., preferably 300-550° C., and more preferably 500° C.

Furthermore, after the reducing step, the method may further include the step of passivating with a nitrogen mixed gas including 1-20% oxygen.

Finally, a carbon-based precious metal-transition metal composite catalyst in which a high-content metal having a uniform composition is supported can be prepared. The catalyst according to the present invention may be in the form of a powder, particles, or granules. Preferably, the catalyst according to the present invention is in the form of a powder.

Hereinafter, preferred examples are presented so as to help the understanding of the present invention. However, the following examples are for illustrative purposes only and the present invention is not limited by the following examples.

EXAMPLES

[Preparation Example 1] Pretreatment of Carbon Support 30 g of a carbon support, 300 g of distilled water, and 300 g of 60% nitric acid solution were sequentially added to a 4-neck flask. The carbon suspension was heated and stirred at 95° C. for 3 hours by using a stirrer equipped with a reflux cooling device, and then cooled to room temperature. The acid-treated carbon suspension was filtered under reduced pressure to obtain a precipitate, and the precipitate was washed to remove remaining organic/inorganic materials. At this time, the filtrate was washed with distilled water several times until pH of the filtrate reached 7. The obtained carbon powder was dried in an oven at 100° C. for 24 hours and used as a catalyst support.

[Example 1] Preparation of Ru—Sn/C Catalyst Using Deposition-Precipitation Method A catalyst preparation apparatus was used by attaching a reflux cooler, a pH electrode, an overhead stirrer, a temperature sensor, and a precipitant injection tube to each branch by using a 5-neck flask with a capacity of 1,000 ml. First, 10 g of the carbon support prepared in Preparation Example 1 and 300 ml of distilled water were added and dispersed in a flask equipped with a reflux cooling device, and then stirred at a temperature of 80° C. for about 1 hour (400 rpm). In order to make a ruthenium-tin precursor solution, 3.9 g of $RuCl_3 \cdot 3H_2O$ and 3.5 g of $SnCl_2 \cdot 2H_2O$ were simultaneously dissolved in 30 ml of 0.05M HCl solution, and then stirred at a rate of 400 rpm for 30 minutes. The ruthenium-tin precursor solution was added to the carbon support dispersion of 80° C. in which the carbon support was dispersed, and then stirred for 1 hour. A precipitant (1M $NH_4OH$) was gradually added to the mixed solution of ruthenium-tin-carbon support (5 cc/min) to adjust final pH to 6, and then stirred and maintained for 1 hour. After the precipitation was complete, the precipitation solution was cooled to room temperature. The recovered precipitate was washed with distilled water of 80° C. or higher to remove remaining organic/inorganic materials. After the washing was completed, the precipitate was dried in a 100° C. convection oven. This was reduced at 500° C. for 3 hours while flowing hydrogen (100 cc/min $H_2$:30/$N_2$:70), and then cooled to room temperature while flowing nitrogen (100 cc/min). After that, a catalyst was prepared by passivating while flowing a 3% oxygen/nitrogen mixed gas (100 cc/min air: 15/N$_2$:85) for 1 hour. The prepared catalyst is denoted by 'Ru—Sn/C-DP'.

[Comparative Example 1] Preparation of Ru—Sn/C Catalyst Using Incipient-Wetness Impregnation Method In order to support ruthenium and tin on a carbon support pretreated with 30 wt % nitric acid, an incipient-wetness impregnation method was performed to dissolve a ruthenium precursor (3.9 g of RuCl$_3$·3H$_2$O) and a tin precursor (3.5 g of SnCl$_2$·2H$_2$O) in distilled water and support the two precursors at once. After that, drying was performed for 12 hours in a 100° C. convection oven. This was reduced at 500° C. for 3 hours while flowing hydrogen (100 cc/min H$_2$:30/N$_2$:70), and then cooled to room temperature while flowing nitrogen (100 cc/min). After that, a catalyst was prepared by passivating while flowing a 3% oxygen/nitrogen mixed gas (100 cc/min air:15/N$_2$:85) for 1 hour. The prepared catalyst is denoted by 'Ru—Sn/C-IWI'.

Figure 2:
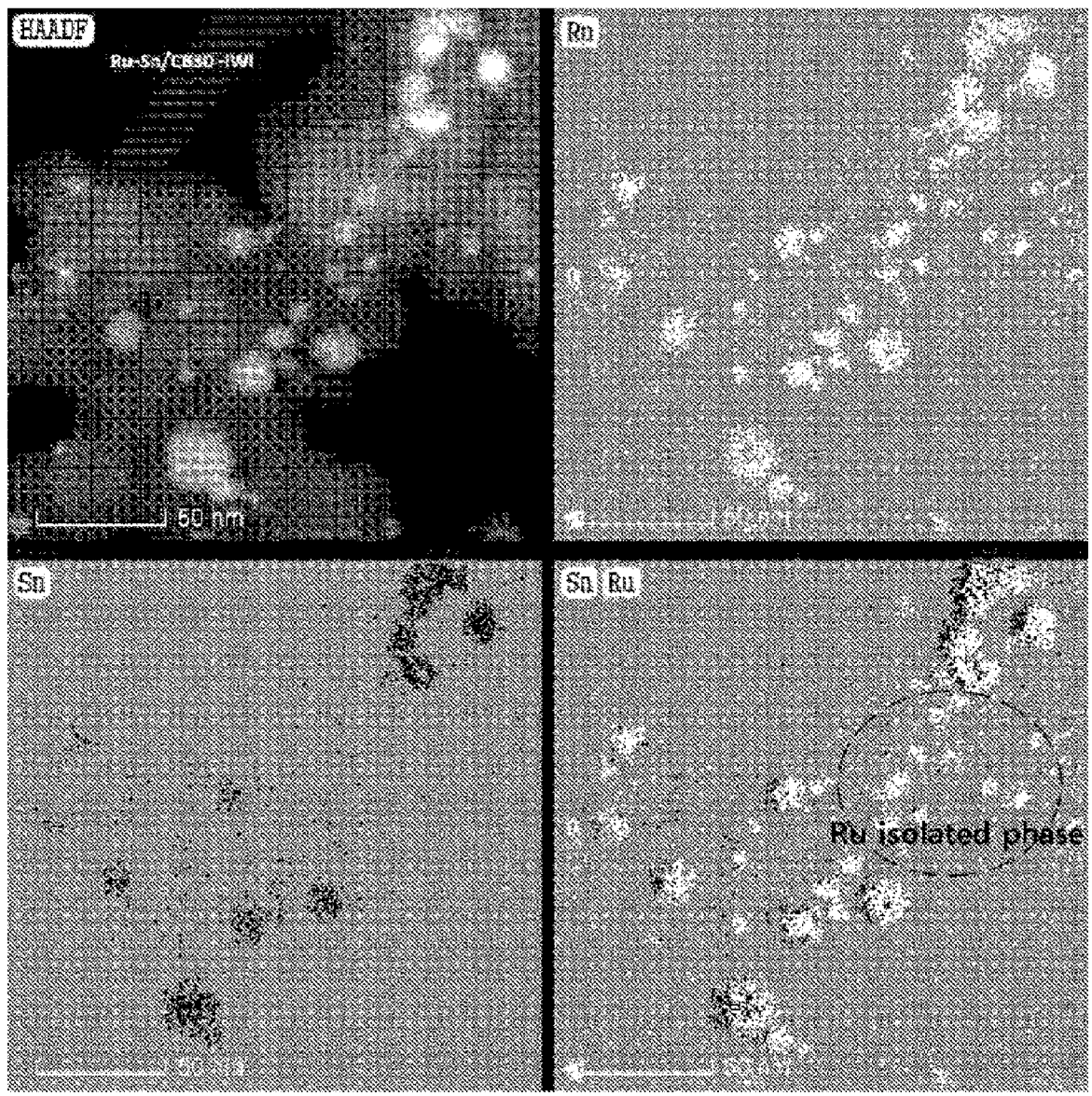
FIG. 2 is a STEM-EDX analysis result of a Ru—Sn/C-IWI catalyst prepared by an incipient-wetness impregnation method according to an embodiment of the present invention.

[Experimental Example 1] Surface Analysis of Ru—Sn/C Catalyst Through STEM-EDX Analysis Transmission electron microscope-energy dispersive X-ray spectroscopy (STEM-EDX) analysis result (STEM-EDX) mapping results of the catalysts prepared in Example 1 and Comparative Example 2 are shown in FIGS. 1 and 2. FIG. 1 shows the STEM-EDX analysis result of the Ru—Sn/C catalyst of Example 1 using the deposition-precipitation method according to the present invention, and FIG. 2 shows the STEM-EDX analysis result of the Ru—Sn/C-IWI catalyst of Comparative Example 1 prepared by the incipient-wetness impregnation method.

[Experimental Example 2] Cyclohexane Dicarboxylic Acid Conversion Experiment

The CHDM conversion experiment was conducted through the hydrogenation reaction of CHDA represented by dicarboxylic acid. This reaction was performed in a batch reactor made of acid-resistant titanium-lined stainless material with a maximum working pressure of 100 bar. A reactant CHDA and the catalyst were injected into the reactor at a weight ratio of 3.75:1, and distilled water was filled as a reaction solvent. At this time, the amount of the reactant relative to the solvent was fixed to 1.6 wt %. After that, the reactor was pressurized to a reaction pressure of 90 bar by using hydrogen, and whether the reactor leaked was checked through a hydrogen detector. Oxygen inside the reactor was completely removed by depressurization and purging. In the hydrogenation reaction, the reactor was heated so that the internal temperature of the reactor reached the reaction temperature (230° C.), and the reactor was pressurized and maintained at the reaction pressure of the hydrogen atmosphere (90 bar). The reaction mixture was stirred at 1,000 rpm for 6 hours using an overhead stirrer. The products by reaction time were sampled through a metal filter. After silylation with N,O-bis(trimethylsilyl) trifluoroacetamide (BSTFA), the products and residual reactants were analyzed using gas chromatography (DS-SCIENCE) with HP-1 column (Agilent). The catalytic activity was compared with the product conversion and yield over time, which are expressed by Equations 1 to 3 below.

$$\text{Conversion of } CHDA \text{ (\%)} = \frac{\text{Mole of } CHDA \text{ Reacted}}{\text{Mole of } CHDA \text{ in the Feed}} \times 100 \quad \text{[Equation 1]}$$

$$\text{Selectivity for } CHDM \text{ (\%)} = \frac{\text{Mole of } CHDM \text{ formed}}{\text{Mole of } CHDA \text{ Reacted}} \quad \text{[Equation 2]}$$

$$\text{Yield for } CHDM \text{ (\%)} = \quad \text{[Equation 3]}$$
$$(\text{Conversion of } CHDA) \times (\text{Selectivity for } CHDM)$$

As a result of the STEM analysis of FIGS. 1 and 2 according to Experimental Example 1, it can be confirmed that in the case of the catalyst prepared by the deposition-precipitation method, ruthenium and tin particles are evenly dispersed on the carbon support. On the EDX, a green dot represents ruthenium and a red dot represents tin. The alloying status can be checked through the EDX result. In the case of the catalyst prepared by the deposition-precipitation method, it can be confirmed that tin (Sn) is mixed at a position where ruthenium (Ru) exists on a single particle identified in an electron image, and it can be determined that ruthenium and tin form a Ru—Sn alloy phase well.

On the other hand, in the case of the catalyst of FIG. 2 prepared by the incipient-wetness impregnation method, a perfect homogeneous phase is not shown and some ruthenium crystals existing independently can be observed, unlike the catalyst prepared by the deposition-precipitation method. Since ruthenium existing independently cannot polarize the carbonyl group, the degree of participation in the reaction decreases. Therefore, it can be determined that the activity is low.

Figure 3:
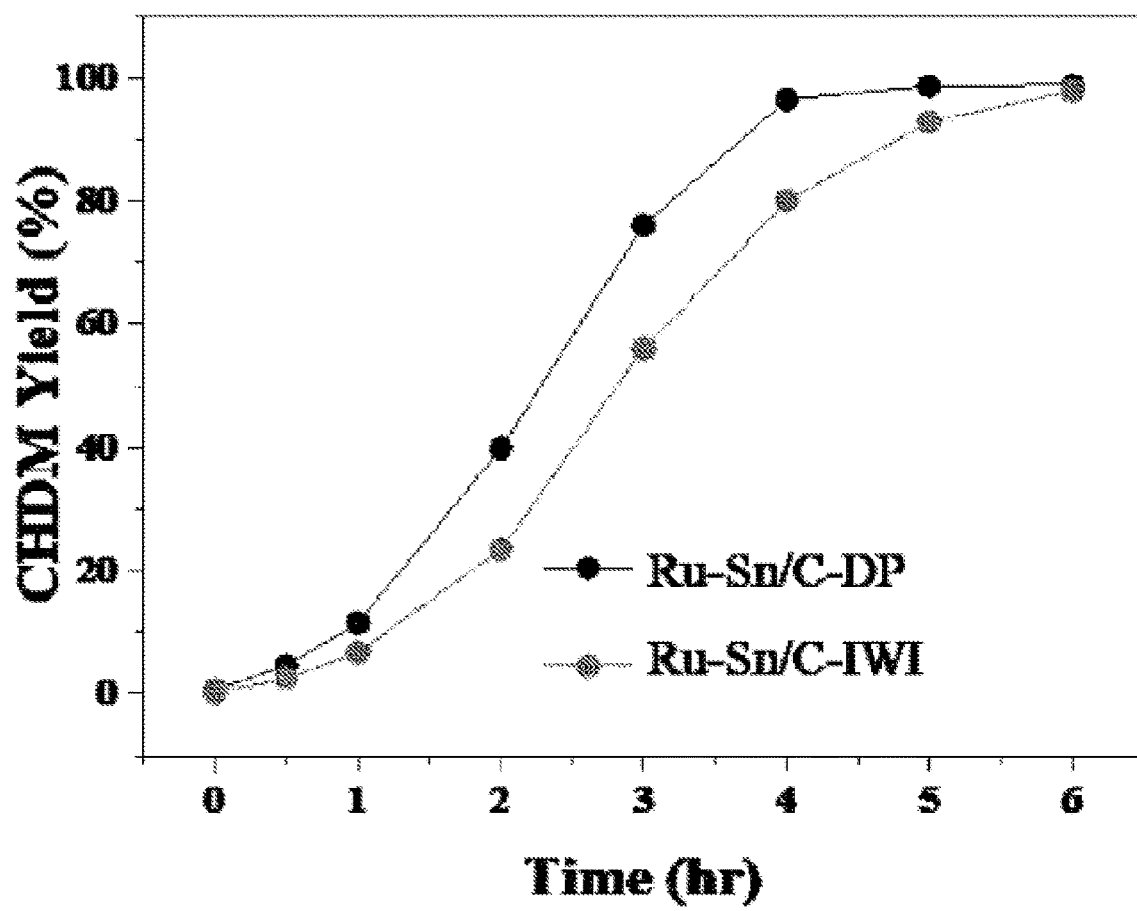
FIG. 3 is a diagram showing a result of evaluating the catalytic activity with the CHDM yield over time.

In addition, in order to compare the performance of the catalyst, the Ru—Sn/C catalysts prepared in Example 1 and Comparative Example 1 were applied to the CHDA hydrogenation reaction [Example 2]. In order to compare the reaction rate of each catalyst, the results of evaluating the catalytic activity with the CHDM yield over time are shown in FIG. 3. As shown in FIG. 3, when compared after 3 hours from the start of the reaction, it was confirmed that the catalyst (Ru—Sn/C-DP) prepared by the deposition-precipitation method showed about 1.5 times superior activity to the catalyst (Ru—Sn/C-IWI) prepared by the incipient-wetness impregnation method. In the heterogeneous catalyst, the reaction is performed on the surface of the active species. Therefore, in the case of the catalysts having the same amount of active species, as the density and uniformity of the active species in the catalyst increase, the activity of the catalyst increases. Therefore, it was confirmed that the catalyst prepared by the deposition-precipitation method showed more excellent activity. Through this, it can be seen that the catalyst prepared by the deposition-precipitation method produces CHDM more efficiently.

Although the present invention has been described with reference to the drawings according to embodiments of the present invention, it will be understood by those of ordinary skill in the art that various applications and modifications can be made thereto without departing from the scope of the present invention.

The invention claimed is:

1. A carbon-based precious metal-transition metal composite catalyst comprising 10-20 parts by weight of the precious metal and 10-20 parts by weight of the transition metal based on 100 parts by weight of the composite catalyst, wherein a total amount of the precious metal-transition metal is 20-40 parts by weight based on 100 parts by weight of the composite catalyst, wherein the precious metal-transition metal forms a homogeneous mixed phase.

2. The carbon-based precious metal-transition metal composite catalyst of claim 1, wherein the precious metal includes one or more selected from the group consisting of palladium (Pd), rhodium (Rh), ruthenium (Ru), and platinum (Pt).

3. The carbon-based precious metal-transition metal composite catalyst of claim 1, wherein the transition metal includes one or more selected from the group consisting of tin (Sn), iron (Fe), rhenium (Re), and gallium (Ga).

4. The carbon-based precious metal-transition metal composite catalyst of claim 1, wherein the precious metal-transition metal is an active metal having a metal crystallite size of 1-20 nm.

5. The carbon-based precious metal-transition metal composite catalyst of claim 1, wherein the precious metal and the transition metal are supported on a support in a range of 0.5-3 moles of the transition metal with respect to 1 mole of the precious metal.

6. The carbon-based precious metal-transition metal composite catalyst of claim 1, wherein an average particle size ($d_{50}$) of the precious metal-transition metal composite catalyst is 3-50 μm.

7. The carbon-based precious metal-transition metal composite catalyst of claim 1, wherein the carbon includes one or more selected from the group consisting of activated carbon, carbon black, graphite, graphene, ordered mesoporous carbon (OMC), and carbon nanotubes.

8. The carbon-based precious metal-transition metal composite catalyst of claim 1, wherein the carbon has a specific surface area of 100-1,500 $m^2/g$ and a pore volume of 0.1-1.5 ml/g.

9. The carbon-based precious metal-transition metal composite catalyst of claim 1, wherein the carbon has ordered mesopores of 2-25 nm.

10. The carbon-based precious metal-transition metal composite catalyst of claim 1, wherein the carbon support is pretreated with an aqueous nitric acid ($HNO_3$) solution, and includes 1-50 parts by weight of nitric acid based on 100 parts by weight of the total aqueous nitric acid ($HNO_3$) solution.

11. The carbon-based precious metal-transition metal composite catalyst of claim 1, wherein the composite catalyst is used in a hydrogenation reaction.

12. The carbon-based precious metal-transition metal composite catalyst of claim 11, wherein the hydrogenation reaction reduces a dicarboxylic acid group to a dialcohol group.

13. The carbon-based precious metal-transition metal composite catalyst of claim 11, wherein the hydrogenation reaction reduces a carboxylic acid functional group, an aldehyde functional group, or a ketone functional group to an alcohol functional group.

14. The carbon-based precious metal-transition metal composite catalyst of claim 13, wherein the carboxylic acid functional group includes one or more selected from the group consisting of oxalic acid, malonic acid, succinic acid, glutaric acid, adipic acid, pimelic acid, suberic acid, azelaic acid, sebacic acid, phthalic acid, isopthalic acid, cyclohexane dicarboxylic acid, and terephthalic acid.

15. A method for preparing a carbon-based precious metal-transition metal composite catalyst, the method comprising the steps of:
(a) preparing a support dispersion in which a carbon support is dispersed in a solvent;
(b) adding a precious metal-transition metal precursor aqueous solution and a precipitant to the support dispersion, supporting a metal oxide or a metal hydrate on the carbon support, and performing precipitating thereon; and
(c) reducing and passivating the precipitate,
wherein the precious metal-transition metal forms a homogeneous mixed phase.

16. The method of claim 15, wherein the precious metal-transition metal composite catalyst includes 10-20 parts by weight of the precious metal and 10-20 parts by weight of the transition metal based on 100 parts by weight of the composite catalyst, and a total amount of the precious metal-transition metal is 20-40 parts by weight based on 100 parts by weight of the composite catalyst.

17. The method of claim 15, wherein the precious metal in the step (b) includes one or more selected from the group consisting of palladium (Pd), rhodium (Rh), ruthenium (Ru), and platinum (Pt).

18. The method of claim 15, wherein the transition metal in the step (b) includes one or more selected from the group consisting of tin (Sn), iron (Fe), rhenium (Re), and gallium (Ga).

19. The method of claim 15, wherein the precipitating in step (b) uses an alkaline solution precipitant, and the precipitant includes one or more selected from the group consisting of hydroxide ($OH^-$), carbonate ($CO_3^{2-}$), and urea.

20. The method of claim 15, wherein a pH is 3-7 when a precipitate is produced in the precipitating in the step (b).

21. The method of claim 15, wherein the reducing in the step (c) is performed in a range of 300-600° C. in a hydrogen atmosphere.

* * * * *